United States Patent [19]

Oka et al.

[11] 4,035,363

[45] July 12, 1977

[54] 1,3-BENZOXAZINE DERIVATIVES

[75] Inventors: Yoshikazu Oka, Kobe; Mitsumi Tomimoto, Kawanishi; Sukehiro Chiba, Kobe, all of Japan

[73] Assignee: Takeda Chemical Industries, Ltd., Osaka, Japan

[21] Appl. No.: 639,461

[22] Filed: Dec. 9, 1975

Related U.S. Application Data

[63] Continuation of Ser. No. 473,297, May 24, 1974, abandoned.

[30] Foreign Application Priority Data

May 28, 1973  Japan .............................. 48-59495

[51] Int. Cl.² ............ C07D 265/00; C07D 273/00; C07D 295/00
[52] U.S. Cl. .......................................... 260/244 R
[58] Field of Search .............................. 260/244 R

[56] References Cited

U.S. PATENT DOCUMENTS

| | | | |
|---|---|---|---|
| 2,806,031 | 9/1957 | Rigterink | 260/244 R |
| 2,811,523 | 10/1957 | Rigterink | 260/244 R |
| 3,825,538 | 7/1974 | Reynolds et al. | 260/244 R |

FOREIGN PATENT DOCUMENTS

| | | | |
|---|---|---|---|
| 598,670 | 5/1970 | Canada | 260/244 |
| 1,445,855 | 12/1968 | Germany | |

OTHER PUBLICATIONS

J. Am. Chem. Soc. 71, 609–612 (1949), W. Burke, "3,4 Dihydro-1,3,2 H Benoxazines, Reaction of - - -".
J. Am. Chem. Soc. 74, 3601–3605 (1952), W. Burke et al., "Condensation of Naphthols - - -".
J. Am. Chem. Soc. 76, 1677–1679 (1954), W. Burke et al., "Condensation of Hydroxyaromatic - - -".
J. of Med. Pharm. Chem. 5(2), pp. 257–280 (1962), Kuehne et al., "Dihydro–1,3 oxazines as Antitumor Agents".

*Primary Examiner*—Albert T. Meyers
*Assistant Examiner*—D. W. Robinson
*Attorney, Agent, or Firm*—Wenderoth, Lind & Ponack

[57] ABSTRACT

Novel compounds of the formula

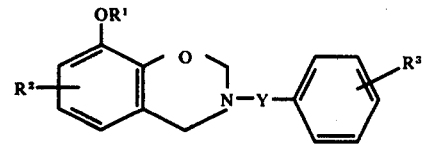

wherein $R^1$ is lower alkyl, $R^2$ is hydrogen, lower alkyl or lower alkenyl, $R^3$ is hydrogen, lower alkyl, lower alkoxy or halogen and Y is lower alkylene.

17 Claims, No Drawings

1,3-BENZOXAZINE DERIVATIVES

This is a continuation of application Ser. No. 473,297, filed May 24, 1974, now abandoned This invention relates to a novel 1,3-benzoxazine derivative of the formula

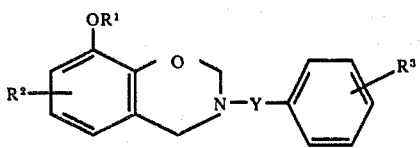

(I)

wherein $R^1$ is lower alkyl, $R^2$ is hydrogen, lower alkyl or lower alkenyl, $R^3$ is hydrogen, lower alkyl, lower alkoxy or halogen and Y is lower alkylene.

The present invention also relates to a novel compound which is represented by the formula:

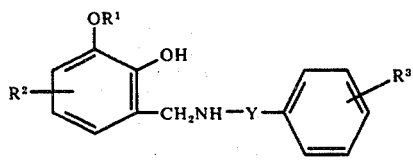

(II)

wherein all the symbols have the meanings as defined above.

The present compounds (I) and (II) are useful for example as an antidepressant, and the latter compound is also useful as an intermediate for the production of the compound (I).

Referring to the symbols of the above formulas, lower alkyl represented by $R^1$ is preferably such one as having 1 to 4 carbon atoms (e.g., methyl, ethyl, propyl, isopropyl, normal butyl, isobutyl or secondary butyl) and particularly ethyl is desirable for the contemplated pharmaceutical action.

The lower alkyl represented by $R^2$ is preferably exemplified by those mentioned for $R^1$ as above. The alkenyl represented by $R^2$ is preferably such one as having 2 to 4 carbon atoms (e.g., vinyl, allyl, isopropenyl, 2-methallyl, 3-methallyl or 3-butenyl). As the group $R^2$, hydrogen is most desirable for the contemplated pharmaceutical action.

The lower alkyl represented by $R^3$ is preferably exemplified by those mentioned as above for $R^1$.

The lower alkoxy represented by $R^3$ is preferably such one as having 1 to 4 carbon atoms (e.g., methoxy, ethoxy, propoxy, isopropoxy, butoxy or isobutoxy). The halogen represented by $R^3$ is for example chlorine, bromine, iodine or fluorine. The halogen or the lower alkoxy which is represented by $R^3$ may be substituted on the phenyl ring in a number of from 1 to 4. As the group $R^3$, hydrogen or chlorine is desirable for the contemplated pharmaceutical action. The lower alkylene represented by Y is preferably such one as having 1 to 4 carbon atoms (e.g., methylene, methylmethylene, ethylene, ethylidene, trimethylene, propylene, propylidene or tetramethylene) and ethylene is most desirable for the contemplated pharmaceutical action.

Principal object of the present invention is to provide the novel compound (I).

Second object is to provide the novel compound (II) useful as an antidepressant and also as an intermediate for the production of the compound (I).

Another object is to provide a process for the production of the compound (I) or the compound (II).

Other objects will be made clear from the following description.

The present compound (I) is produced by allowing a compound of the formula

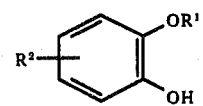

(III)

wherein all the symbols have the meanings as defined above, to react with formaldehyde and a compound of the formula

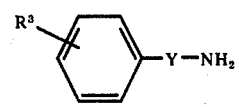

(IV)

wherein all the symbols have the meanings as defined above.

The above reaction is considered to proceed through the formation of the intermediate (II), with which formaldehyde reacts to yield the compound (I).

Formaldehyde is employed in an amount of not less than 2 mols per mol of the compound (III) and practically below about 5 mols on the same basis. The compound (IV) is employed in an amount of not less than 1 mol of the compound (III) and practically below about 5 mols on the same basis. The intermediate (II) may be taken out of the reaction mixture when the reaction proceeds not so rapidly. Accordingly the present compound (I) is produced by reacting the compound (II) with formaldehyde. In such a case, formaldehyde is employed in an amount of at least 1 mol relative to 1 mol of the compound (II).

As formaldehyde, there may be employed such compounds as function equally to formaldehyde in the present reaction. Such compounds are exemplified by polymers of formaldehyde (e.g., paraformaldehyde or trioxymethylene) or dialkoxymethane (e.g., dimethoxymethane or diethoxymethane).

The present reaction is generally conducted in an inert solvent (e.g., methanol, ethanol, ethyl acetate, chloroform, dioxane, ethyl ether or benzene). The reaction temperature is suitably selected from about −5° to 200° C, preferably about 80° to 150° C.

The compound (I) and the compound (II) can be taken out of the reaction mixture by per se conventional isolation procedures, for example, distillation, extraction, crystallization or column chromatography.

The compound (I) and (II) can be recovered as their acid addition salts with inorganic acids (e.g., hydrochloric acid, sulfuric acid or phosphoric acid) or organic acids (e.g., oxalic acid, maleic acid, fumaric acid, methanesulfonic acid, benzenesulfonic acid, toluenesulfonic acid, naphthalenesulfonic acid or ascorbic acid).

The compound (I) and the compound (II) are useful as antidepressants for human beings and other mammals (e.g., rat, monkey or the like). Those compounds may be administered orally or parenterally. The compounds may be administered as such or in a form of powder, granules, capsules, tablets, aqueous solution or injection which are prepared by per se conventional procedure. Dosage can be determined dependent upon the disease to be treated, each host, etc., and is generally selected from about 1 to 14 mg/kg of body weight daily for oral route and about 0.6 to 6 mg/kg of body weight daily by injection, when they are administered to adult human for the treatment of depression.

EXAMPLE 1

To 20 ml. of dioxane are added 6 ml. of 37% of formalin and 4.8 g. of phenethylamine. Then, a solution of 5 g. of orthomethoxyphenol in 6 ml. of dioxane is added. The mixture is heated on reflux for 5 hours, after which the solvent is distilled off under reduced pressure. The residue is purified by column chromatography on silica gel (acetone : benzene = 1 : 30) to obtain an oil. This product is dissolved in ether and, then, an ethereal solution of para-toluene-sulfonic acid is added.

The ether is decanted off and 30 ml. of water is added, followed by stirring. The crystals which will have separated out are collected by filtration. The procedure yields 11 g. of 8-methoxy-3-phenethyl-3,4-dihydro-2H,1,3-benzoxazine paratoluenesulfonate which melts at 145°–148° C.

Elemental analysis, for $C_{24}H_{27}NO_5S.H_2O$ (%).
Calcd. C, 62.73; H, 6.37; N, 3.05.
Found C, 62.74; H, 6.18; N, 2.88.

The oily product is dissolved in ether, and to the solution is added an ethereal solution of oxalic acid. The mixture is allowed to stand and the crystals that will have separated are harvested by filtration. In this case, there is obtained 8-methoxy-3-phenethyl-3,4-dihydro-2H-1,3-benzoxazine oxalate which melts at 188°–189° C.

Elemental analysis, for $C_{19}H_{21}NO_6$ (%).
Calcd. C, 63.50; H, 5.89; N, 3.90.
Found C, 62,47; H, 5.90; N, 3.97.

EXAMPLE 2

To 10 ml. of dioxane are added 3 ml. of 37% formalin and 2.42 g. of phenethylamine. Then, a solution of 2.76 g. of orthoethoxyphenol in 3 ml. of dioxane is added. The mixture is heated on reflux for 5 hours, after which the solvent is distilled off under reduced pressure. Cold ethanol is added to the solid residue, which is then harvested by filtration. The procedure yields 4.4 g. of 8-ethoxy-3-phenethyl-3,4-dihydro-2H-1,3-benzoxazine which melts at 88°–90° C.

Elemental analysis, for $C_{18}H_{21}NO_2$ (%).
Calcd. C, 76.29; H, 7.47; N, 4.94.
Found C, 76.06; H, 7.46; N, 4.86.

EXAMPLE 3

To 10 ml. of dioxane are added 3 ml. of 37% formalin and 2.14 g. of benzylamine. Then, a solution of 2.5 g. of orthomethoxyphenol in 3 ml. of dioxane is added. The reaction mixture is heated on reflux for 5 hours, after which the solvent is distilled off under reduced pressure. The oily residue is then purified by column chromatography on silica gel (acetone : benzene = 1 : 30) and the resultant oil is allowed to stand at room temperature. The crystals that will have separated out are collected by filtration to obtain 1.5 g. of 3-benzyl-8-methoxy-3,4-dihydro-2H-1,3-benzoxazine which melts at 76°–77° C.

Elemental analysis, for $C_{16}H_{17}NO_2$ (%).
Calcd. C, 75.27; H, 6.71; N, 5.49.
Found C, 75.34; H, 6.72; N, 5.49.

EXAMPLE 4

To 10 ml. of dioxane are added 3 ml. of 37% formalin and 3.7 g. of 3,4-dimethoxyphenethylamine. Then, a solution of 2.5 of ortho-methoxyphenol in 3 ml. of dioxane is added. The reaction mixture is heated on reflux for 5 hours, after which time the solvent is distilled off under reduced pressure. The oily residue is purified by column chromatography on silica gel (acetone : benzene = 1 : 4), and ether is added to the resultant oil. Stirring the mixture causes crystals to separate. These crystals are collected by filtration. The procedure yields 4.5 g. of 8-methoxy-3-(3,4-dimethoxyphenethyl)-3,4-dihydro-2H-1,3-benzoxazine, melting point: 101°–102° C.

Elemental analysis, for $C_{19}H_{23}NO_4$ (%).
Calcd. C, 69.28; H, 7.04; N, 4.25.
Found C, 69.15; H, 7.11; N, 4.14.

EXAMPLE 5

To 10 ml. of dioxane are added 3 ml. of 37% formalin and 2.7 g. of 3-phenylpropylamine. Then, a solution of 2.5 g. of orthomethoxyphenol in 3 ml. of dioxane is added. The reaction mixture is heated on reflux for 5 hours, after which the solvent is distilled off under reduced pressure. The oily residue is purified by column chromatography on silica gel (acetone : benzene = 1 : 30). The resultant oil is dissolved in ether and an ethereal solution of para-toluenesulfonic acid is added. The mixture is stirred and the crystals which will have separated are collected by filtration. The procedure yields 7.15 g. of 8-methoxy-3-(3-phenyl-propyl)-3,4-dihydro-2H-1,3-benzoxazine para-toluenesulfonate which melts at 119°–121° C.

Elemental analysis, for $C_{25}H_{29}NO_5S.H_2O$ (%).
Calcd. C, 63.40; H, 6.62; N, 2.96.
Found C, 63.29; H, 6.86; N, 2.80.

EXAMPLE 6

To 10 ml. of dioxane are added 3 ml. of 37% formalin and 2.42 g. of phenethylamine. Then, a solution of 2.76 g. of 2-methoxy-4-methylphenol in 3 ml. of dioxane is added. The reaction mixture is heated on reflux for 5 hours, after which the solvent is distilled off under reduced pressure. The oily residue is purified by column chromatography on silica gel (acetone : benzene = 1 : 30). The resultant oily product is dissolved in ether and an ethereal solution of para-toluenesulfonic acid is added. The crystals that will have separated are collected by filtration. The procedure yields 5.25 g. of 8-methoxy-6-methyl-3-phenethyl-3,4-dihydro-2H-1,3-benzoxazine para-toluenesulfonate which melts at 108°–110° C.

Elemental analysis, for $C_{25}H_{29}NO_5S.H_2O$ (%).
Calcd. C, 63.40; H, 6.62; N, 2.96.
Found C, 63.33; H, 6.58; N, 3.03.

EXAMPLE 7

To 10 ml. of dioxane are added 3 ml. of 37% formalin and 2.4 g. of DL-α-methylbenzylamine. Then, a solution of 2.5 g. of ortho-methoxyphenol in 3 ml. of dioxane is added.

The reaction mixture is heated on reflux for 5 hours, after which the solvent is distilled off under reduced pressure. To the residue are added ethanol and petroleum ether and the mixture is filtered to obtain 4.2 g. of 8-methoxy-3-(α-methylbenzyl)-3,4-dihydro-2H-1,3-benzoxazine, melting point: 99°–101° C.

Elemental analysis, for $C_{17}H_{19}O_2N$ (%).
Calcd. C, 75.81; H, 7.11; N, 5.20.
Found C, 74.92; H, 7.16; N, 5.22.

EXAMPLE 8

To 10 ml. of dioxane are added 3 ml. of 37 % formalin and 2.42 g. of phenethylamine. Then, a solution of 3.28 g. of ortho-methoxyphenol in 3 ml. of dioxane is added. The reaction mixture is heated on reflux for 5 hours, after which the solvent is distilled off. The oily residue is then purified by column chromatography on silica gel (acetone : benzene = 1 : 30). The resultant oil is dissolved in ether, and an ethereal solution of para-toluenesulfonic acid is added, followed by stirring. The crystals that will have separated are harvested by filtration. The procedure gives 6.9 g. of 6-allyl-3-phenethyl-8-methoxy-3,4-dihydro-2H-1,3-benzoxazine para-toluenesulfonate which melts at 144°–146° C.

Elemental analysis, for $C_{27}H_{31}O_5NS \cdot H_2O$ (%).
Calcd. C, 65.17; H, 6.28; N, 2.82.
Found C, 66.08; H, 6.40; N, 2.72.

EXAMPLE 9

1. To 10 ml. of dioxane are added 1.5 ml. of 37% formalin and 2.42 g. of phenethylamine. Then, a solution of orthoethoxyphenol in 3 ml. of dioxane is added. The reaction mixture is heated on reflux at 110°–120° C for 4 hours, after which time the solvent is distilled off under reduced pressure. The oily residue is purified by column chromatography on silica gel (acetone : benzene = 1 : 4), and petroleum ether is added to the resultant solid. The mixture is filtered to obtain 0.8 g. of 2-ethoxy-6-phenethylaminomethylphenol which melts at 72°–73° C.

Elemental analysis, for $C_{17}H_{21}O_2N$ (%).
Calcd. C, 75.24; H, 7.80; N, 5.16.
Found C, 75,23; H, 7.80; N, 5.18.

2. To 5 ml. of dioxane is added 0.54 g. of the 2-ethoxy-6-phenethylaminomethylphenol obtained according to (1) above, together with 0.2 ml. of 37% formalin. The reaction mixture is heated on reflux for 3 hours, after which the solvent is distilled off. To the solid residue is added cold ethanol, followed by filtration. The procedure yields 0.4 g. of 8-ethoxy-3-phenethyl-3,4-dihydro-2H-1,3-benzoxazine which melts at 88°–90° C.

Elemental analysis, for $C_{18}H_{21}O_2N$ (%).
Calcd. C, 76.29; H, 7.47; N, 4.94.
Found C, 76.18; H, 7.45; N, 4.88.

EXAMPLE 10

1. To 10 ml. of dioxane are added 1.5 ml. of 37% formalin and 2.42 g. of phenethylamine, followed by the addition of 3.2 g. of ortho-methoxyphenol dissolved in 3 ml. of dioxane. The mixture is heated at 100° C for 4 hours and distilled under reduced pressure to remove the solvent. The residue is purified by column chromatography on silica gel with a mixture of acetone and benzene (1:4) to obtain 2-methoxy-6-phenethylaminomethylphenol as an oil. Yield: 0.7 g.

The product obtained above is dissolved in ether and an ethereal solution of para-toluenesulfonic acid is added, whereupon para-toluenesulfonic acid salt of the compound is separated as crystals. Recrystallization from hot water yields colorless prisms melting at 158°–160° C.

Elemental analysis for $C_{23}H_{27}O_5NS$ (%).
Calcd. C, 64.31; H, 6.34; N, 3.26.
Found C, 64.36; H, 6.15; N, 3.66.

2. To 5 ml. of dioxane are added 0.6 g. of 2-methoxy-6-phenethylaminomethylphenol prepared as above and 1 ml. of 37% formalin. The mixture is heated on reflux for 3 hours and distilled to remove the solvent. The residue is purified by column chromatography on silica gel with a mixture of acetone and benzene (1:4). The resultant oil is left standing at cool place for 2–3 days to be solidified. Recrystallization from normal hexane yields 8-methoxy-3-phenethyl-3,4-dihydro-2H-1,3-benzoxazine as colorless needles melting at 63°–66° C. Yield: 0.4 g.

Elemental analysis for $C_{17}H_{19}O_2N$ (%).
Calcd. C, 75.81; H, 7.11; N, 5.20.
Found C, 75.77; H, 6.90; N, 5.13.

EXAMPLE 11

To 120 ml. of dioxane are added 5 g. of ortho-methoxyphenol, 9 ml. of 37% formalin and 7.56 g. of ortho-chlorophenethylamine. The mixture is heated on reflux for 3 hours and distilled to remove the solvent. The residue is purified by column chromatography on silica gel with a mixture of acetone and benzene (1:4). The resultant oil is cooled to be solidified. Recrystallization from methanol yields 3-(2-chlorophenethyl)-8-methoxy-3,4-dihydro-2H-1,3-benzoxazine as colorless needles melting at 79°–81° C. Yield: 6 g.

Elemental analysis for $C_{17}H_{18}O_2NCl$ (%).
Calcd. C, 67.21; H, 5.97; N, 4.61.
Found C, 67.26; H, 5.88; N, 4.48.

EXAMPLE 12

To 20 ml. of dioxane are dissolved 5 g. of orthomethoxyphenol, 5 g. of para-formaldehyde and 12.6 g. of para-chlorophenethylamine. The solution is heated on reflux for 9.5 hours and distilled to remove the solvent. The residue is purified by column chromatography on silica gel with a mixture of acetone and benezene (1:4). Recrystallization of the resultant crude crystals from methanol yields 3-(4-chlorophenethyl)-8-methoxy-3,4-dihydro-2H-1,3-benzoxazine as colorless needles melting at 87°–88° C. Yield: 4 g.

Elemental analysis for $C_{17}H_{18}O_2NCl$ (%).
Calcd. C, 67.21; H, 5.97; N, 4.61.
Found C, 67.29; H, 5.99; N, 4.57.

EXAMPLE 13

To 20 ml. of benzene are added 5g. of ortho-methoxyphenol, 9ml. of 37% formalin and 6.5 g. of para-methylphenethylamine. The mixture is heated on reflux for 10 hours and concentrated to dryness under reduced pressure. The residue is purified by column chromatography on silica gel with a mixture of acetone and benzene (1:4). The resultant oil is left standing at cool place for a week to be solidified. Recrystallization from normal hexane yields 8-methoxy-3-(4-methylphenethyl)-3,4-dihydro-2H-1,3-benzoxazine as colorless needles melting at 58°–63° C. Yield: 1.2 g.

Elemental analysis for $C_{18}H_{21}O_2N$ (%).
Calcd. C, 76.29; H, 7.47; N, 4.94.
Found C, 76.20; H, 7.41; N, 5.09.

EXAMPLE 14

To 20 ml. of dioxane are added 5 g. of ortho-methoxyphenol, 9 ml. of 37% formalin and 6.7 g. of para-methoxyphenethylamine. The mixture is heated on reflux for 4 hours and concentrated to dryness under reduced pressure. The residue is purified by column chromatography on silica gel with a mixture of acetone and benzene (1:4). The resultant oily substance is left standing at cool place for one month to be solidified. Recrystallization from petroleum ether yields 8-methoxy-3-(4-methoxyphenethyl)-3,4-dihydro-2H-1,3-benzoxazine as melting at 69°–70° C.

Elemental analysis for $C_{18}H_{21}O_3N$ (%).
Calcd. C, 72.21; H, 7.07; N, 4.68.
Found C, 72.30; H, 7.01; N, 4.15.

EXAMPLE 15

To 15 ml. of dioxane are added 3 g. of ortho-normal-propoxyphenol, 9 ml. of 37% of formalin and 2.4 g. of phenethylamine. The mixture is heated on reflux for 3 hours and distilled to remove the solvent under reduced pressure. The residue is purified by column chromatography on silica gel with a mixture of acetone and benzene (1:4). The resultant oily substance is cooled to be crystallized. A small portion of ethanol is added to the crystals, followed by filtration. The procedure yields 3-phenethyl-8-normal-propoxy-3,4-dihydro-2H-1,3-benzoxazine as colorless needless melting at 84° C. Yield: 3.8 g.

Elemental analysis for $C_{19}H_{23}O_2N$ (%).
Calcd. C, 76.73; H, 7.80; N, 4.71.
Found C, 76.51; H, 8.07; N, 4.47.

We claim:
1. A compound of the formula

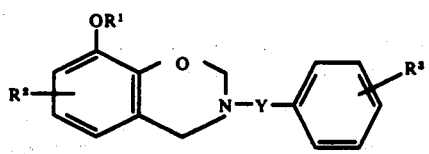

wherein $R^1$ is alkyl of 1 to 4 carbon atoms; $R^2$ is hydrogen, alkyl of 1 to 4 carbon atoms. or alkenyl of 2 of 4 carbon atoms; $R^3$ is hydrogen, alkyl of 1 to 4 carbon atoms, alkoxy of 1 to 4 carbon atoms or halogen and Y is alkylene of 1 to 4 carbon atoms or its pharmaceutically acceptable salts.

2. The compound as claimed in claim 1, wherein $R^1$ is ethyl.
3. The compound as claimed in claim 1, wherein $R^2$ is hydrogen.
4. The compound as claimed in claim 1, wherein $R^3$ is hydrogen or chlorine.
5. The compound as claimed in claim 1, wherein Y is ethylene.
6. The compound as claimed in claim 1, wherein the compound is 8-methoxy-3-phenthyl-3,4-dihydro-2H-1,3-benezoxazine.
7. The compound as claimed in claim 1, wherein the compound is 8-ethoxy-3-phenethyl-3,4-dihydro-2H-1,3-benzoxazine.
8. The compound as claimed in claim 1, wherein the compound is 3-benzyl-8-methoxy-3,4-dihydro-2H-1,3-benzoxazine.
9. The compound as claimed in claim 1, wherein the compound is 8-methoxy-3-(3,4-dimethoxyphenethyl)-3,4-dihydro-2H-1,3-benzoxazine.
10. The compound as claimed in claim 1, wherein the compound is 8-methoxy-3-(α-methylbenzyl)-3,4-dihydro-2H-1,3-benzoxazine.
11. The compound as claimed in claim 1, wherein the compound is 6-allyl-3-phenethyl-8-methoxy-3,4-dihydro-2H-1,3-benzoxazine.
12. The compound as claimed in claim 1, wherein the compound is 8-methoxy-3-(4-methoxyphenethyl)-3,4-dihydro-2H-1,3-benzoxazine.
13. The compound as claimed in claim 1, wherein the compound is 3-phenethyl-8-propoxy-3,4-dihydro-2H-1,3-benzoxazine.
14. The compound as claimed in claim 1, wherein the compound is 8-methoxy-3-phenethyl-3,4-dihydro-2H-1,3-benzoxazine.
15. The compound as claimed in claim 1, wherein the compound is 3-(2chlorophenethyl)-8-methoxy-3,4-dihydro-2H-1,3-benzoxazine.
16. The compound as claimed in claim 1, wherein the compound is 3-(4-chlorophenethyl)-8-methoxy-3,4-dihydro-2H-1,3-benzoxazine.
17. The compound as claimed in claim 1, wherein the compound is 8-methoxy-3-(4-methylphenethyl)-3,4-dihydro-2H-1,3-benzoxazine.

* * * * *